United States Patent [19]

Liedtke

[11] Patent Number: 5,496,560
[45] Date of Patent: Mar. 5, 1996

[54] BORDERLINE ACTIVE DOSAGE FORMS OF BETA BLOCKERS

[75] Inventor: Rainer K. Liedtke, Gruenwald, Germany

[73] Assignee: Pharmed Dr. Liedtke GmbH, Gruenwald, Germany

[21] Appl. No.: 322,420

[22] Filed: Oct. 13, 1994

[30] Foreign Application Priority Data

Oct. 13, 1993 [DE] Germany .......................... 43 34 919.6

[51] Int. Cl.⁶ ............................. A61F 13/00; A61K 9/20
[52] U.S. Cl. ........................... 424/449; 424/464; 514/821
[58] Field of Search ..................................... 424/464, 465, 424/443, 449; 514/821

[56] References Cited

PUBLICATIONS

Facts and Comparisons, Sewester et al., J. B. Lippincott Co., Jan. 1993, p. 158r.
Facts and Comparisons, Kastrup et al., J. B. Lippincott Co., Apr. 1985, pp. 158H–159.

*Primary Examiner*—Thurman K. Page
*Assistant Examiner*—James M. Spear
*Attorney, Agent, or Firm*—Oblon, Spivak, McClelland, Maier & Neustadt

[57] ABSTRACT

For short-term therapy of transient functional cardiovascular symptoms, borderline active dosage forms of beta blockers are used which produce in the body only the borderline active concentrations of active ingredient which produce no significant changes in the physiological values in the cardiovascular system under resting conditions for the respective specific beta blocker used and significantly reduce adrenergically induced transient stimulation effects. Oral, transdermal, or topical dosage forms are particularly advantageous. A differentiated therapy of functional symptoms which does not exist with the customary dosage forms of beta blockers designed for long-term therapies is possible. Both the quality of life and the risk-benefit ratio of the beta blockers are improved. The duration of the therapy also does not have to be extended beyond the symptomatically required scale since no rebound danger exists after withdrawal. As an additional and now indication, this also permits the short-term use for the primary therapy of sleep disturbances, within the framework of vegetative syndromes, in particular, within the framework of postmenopausal symptoms.

8 Claims, No Drawings

BORDERLINE ACTIVE DOSAGE FORMS OF BETA BLOCKERS

BACKGROUND OF THE INVENTION

1. Field of the Invention

The present invention concerns borderline active dosage forms of beta blockers for short-term therapy of transient functional cardiovascular symptoms.

2. Background of the Invention

It is known that the chemical group of beta receptor blockers are part of the standard long-term therapy of manifest cardiovascular disorders such as hypertension and angina pectoris. The application spectrum of beta blockers also includes the following indications: hyperkinetic heart syndrome, migraines, tremors, glaucoma, anxiety syndromes, and withdrawal syndromes. See H. Lydtin & P. Trenkwalder, New Indications for Therapy with Beta-Receptor Blockers in: Beta-Receptor Blockers, G. Fischer, Stuttgart, 1991, pp. 58ff, incorporated herein by reference.

Cardiovascular disorders can be subdivided diagnostically into those with pathological manifestations (e.g., angina pectoris based an a manifest coronary heart disorder), and into symptomatic types with only transient pathological-manifestations without a pronounced morphologic basis (e.g., situation-related reactive accelerations of the heart rate through exogenous or endogenous physical or psychological stressors). Also classified within this area, in a broader sense, are, for example, transient cardiac ischemias: so-called silent myocardial ischemic episodes which are not noticed by the patient but can be seen in the EKG. Transient manifestations of this type are also referred to as functional or vegetative symptoms and are based primarily on situationally inadequate reactions of the sympathetic nervous system or the adrenergic neurotransmitters released by it.

However, in principle, this diagnostic subdivision comprises therapeutically different objectives and thus imposes different requirements for the beta blocker therapy which basically must take into account the fact that in the vegetative patients it is a matter of largely organically healthy individuals. Consequently, this includes differences in the desired duration of treatment, in the different level of intensity of the therapeutic effect, and different dosing requirements as well as a different evaluation of the associated therapeutic risk-benefit ratio.

Currently available dosage forms of, as well as dosage schemes with, beta blockers in no way take these therapeutically different requirements into account. Thus, identical dosage forms are used without differentiation for the therapy of transient vegetative symptoms even though they were designed for long-term therapy of manifest cardiovascular disorders. There is merely an attempt to adapt, somewhat superficially (e.g., through recommendations to use the minimum doses in the range), within the framework of the dosage spectrum already available for the manifest and chronic syndromes. Nonetheless, this is still done using the same dosing frequencies.

In symptomatic patients with transient cardiovascular reactions, use of the dosage forms of beta blockers as occurs in the therapy of chronic cardiovascular patients is fundamentally a pharmacodynamically unnecessary overdose, with an increased risk of adverse effects.

The entire spectrum of currently available dosage forms of beta blockers desired for long-term therapy reduces, among other things, the overall physical performance capability and affects, for example, lipid and glucose metabolism. See M. Wickelmayr at al., Glucose Metabolism and β-Blockers, Diuretics and Calcium-Antagonists, pp. 29–33, in: Effects of Antihypertensive Treatment on Glucose Metabolism, International Symposium Bühlerhohe 1988, Thieme, Stuttgart—New York 1990, incorporated herein by reference. Since, pharmacokinetically, these dosage forms already cause complete saturation of adrenergic receptors from the outset, the first dose usually already leads, through competitive displacement of endogenous catecholamine, to a long-lasting change of the resting parameters of the cardiovascular system. This is not merely unnecessary for transient vegetative symptoms, but is in fact harmful.

As a consequence, with administration of these customary dosage forms, patients with transient symptoms must also again be gradually withdrawn from this type of beta blocker therapy in order not to be subject to the risk of cardiovascular withdrawal phenomena—so-called rebounds, such as reactive increases in heart rate. Consequently, this imposes a longer than necessary use of beta blockers for these transient symptoms.

All acutely excessive reactions of the sympathetic nervous system to physical and psychological stressors as well as all vegetative individual symptoms which are embedded in various syndromes are vegetative syndromes. For example, even sleep disturbances can be included among the latter. These seriously stressful vegetative symptoms have, however, not been amenable to beta blocker therapy, because of the inappropriate dosage forms and are consequently treated with other therapies. Thus, the primary therapy of sleep disturbances currently uses drugs which act an the central nervous system, primarily drugs from the chemical group of benzodiazepines, as well as derivatives of barbituric acid. Such treatments present quite significant disadvantages. The sedative effects are not only pronounced but also clearly extend, as residual effects, into the daytime phases of physical activities. These include excessive daytime sleepiness and reduction of functional reactivity and attentiveness. These substances also have a significant addiction potential. Withdrawal after repeated administration frequently triggers adverse effects and vegetative disorders are even intensified, which the patients then wish to prevent with further continuation of this therapy.

There is as yet no use of beta blockers for primary therapy of sleep disturbances. This is also not unexpected since with the dosage forms of beta blockers currently in use, sleep disturbances and nightmares actually are among the adverse effects of these therapies. These undesirable side effects must however be attributed, among other things, to the excessively persistent cardiovascular effects of the customary dosage forms of beta blockers. In particular, the lipophilic beta blockers, which penetrate the CNS barriers more readily, lead to particularly pronounced sleep disturbances. See A. Wasterland, Central Nervous System Side Effects with Hydrophilic and Lipophilic Beta Blockers, Eur. J. Clin. Pharmacol. (1985) 23 (Suppl.) 73–76, incorporated herein by reference.

Such adverse side effects also cannot be improved with customary time-released forms of beta blockers, which, for example, are intended to enable a single daily administration. Instead, side-effects are further worsened with such time-released forms since, for pharmacokinetic reasons, these must be dosed even higher to achieve a prolonged persistence of the cardiovascular effects. Extensions of the effects on the vegetative parameters more sensitive to beta blockers, in particular on cardiac chronotropy, are however unnecessary for vegetative symptoms. Thus, the pharmacokinetic half life of the beta blockers, analytically determined only from the plasma concentration, is far shorter than its pharmacodynamic active period. The demonstrable reductions in the heart rate persist well beyond the pharmacokinetic parameters without any therapeutic consequence having been derived for the vegetative parameters.

Scattered reports in the literature point to the fact that in addition to the central nervous causes, peripheral factors may also be implicated in sleep disturbances. Thus, various sleep disturbances clearly coincide with transient vegetative reactions. In poor sleepers, it is possible to detect, in addition to elevated body temperature caused by the central nervous system, elevated secretion of the catecholamines epinephrine and norepinephrine. See K. Adam, in: IHindmarch, H. Ott, Th. Roth (Eds.), Sleep, Benzodiazepines and Performance, Springer, Berlin, 1984, 44– 53, incorporated herein by reference. Comparable processes also seem to be present within the framework of female menopause. Thus, significantly increased sleep disturbances occur in this phase characterized by numerous vegetative functional disorders, in particular appearing within the framework of characteristic hot flashes. See D. Sturdee & M. Brincat in: J. Studd, M. Whitehead (Eds.), The Menopause, Blackwell, Oxford, 1988, pp. 24–42, incorporated herein by reference.

Adrenergically induced cardiac manifestations such as tachycardia appear to intensify anxiety attacks. The occurrence of transient anxiety symptoms after experimental adrenergic stimulation in healthy subjects, for example, with intravenous isoprenaline, is known in human pharmacology.

Consequently, from the aforementioned aspects, a reduction of excessive adrenergic stimulation temporarily affecting the heart seems possible as a principle not applied to date in sleep disturbances. The point of action here is the blockade of sleep-disrupting stress factors caused by the central nervous system. This occurs in particular through the chronotropic adrenergic cardiac receptors especially sensitive to beta blockers. The reactive increase in heart rate triggered by the central nervous system is thus prevented and, at the same time, a negative reinforcement on the central nervous system is averted by blockade of the cardiac feedback reaction. Consequently, this leads to the interruption of a circuit developing between the central nervous system and the heart.

However, for a suitable therapy of transient vegetative symptoms with beta blockers, only reductions of nonphysiological adrenergic simulation effects are reasonable with the functional disturbances. In contrast, after these temporary situations subside, persistent long-term effects of the beta blockers on the cardiovascular system, in particular persistent effects on physiological base values of the cardiovascular system, are unnecessary and undesirable. They merely manifest themselves in the reduction of performance and negatively affect the quality of life. Consequently, from a pharmacological standpoint, only a standby situation is required, whereby the pharmacodynamic effect of the beta blocker dosage form is expressed only under stimulation conditions.

Within the framework of various clinical studies with a transdermal system with the beta blocker mepindolol in angina pectoris patients, it was possible to detect serum concentrations of the beta blocker which were lower by a factor of 5 than is the case with the customary therapeutic doses with customary oral application with this beta blocker. With this extraordinarily low concentration of active ingredient, there were differentiated effects on the heart rate. It turned out, as was objectively demonstrated with continuous 24-hour EKGs, that the maximum increases of the heart rate dropped significantly, but the minimum resting rates remained unchanged. This was also accompanied by a significant reduction in silent myocardial ischemic episodes of these patients, thus an improvement in their continuous cardiac circulation. These effects were also successfully reproduced for even shorter applications, e.g., 12-hour applications. See J. Bonelli, P. Gaza, P. Kirsch, R. K. Liedtke, Int. J. Clin. Pharmacal. Therap. Toxicol. 29, 425–430 (1991), incorporated herein by reference.

Thus, the possibility exists to counter functional and transient stimulation phases of the adrenergic system even for a short time without at the same time affecting the basal vegetative homeostasis of the cardiovascular system. In contrast to this, with the use of all dosage forms of beta blockers currently in therapeutic use, even with test subjects with healthy circulation, there are always persistent and significant drops in the physiological resting values of the cardiovascular system, which is associated with a general reduction of physical performance capability.

OBJECTS OF THE INVENTORS

One object of the present invention is to enable short-term therapies of transient functional cardiovascular symptoms with beta blockers and to improve the therapy of functional cardiovascular syndromes as a whole. Other objects will become apparent as the invention becomes better understood with reference to the following summary and detailed description.

SUMMARY OF THE INVENTION

The objects of the present invention are accomplished by providing and using dosage forms of beta blockers which produce in the body only those borderline active concentrations of active ingredient which produce, for the respective specific beta blocker used, no significant changes of the physiological values in the cardiovascular system under resting conditions and significantly reduce adrenergically induced transient stimulation effects from a pharmacodynamic standpoint. The dosage forms may be transdermal or topical dosage forms, etc.

DETAILED DESCRIPTION OF THE INVENTION

To expand the therapy potentials for these borderline active dosage forms of beta blockers, the primary therapy of sleep disturbances within the framework of functional syndromes is added as a new medical indication for beta blockers, whereby this also includes the sleep disturbances within the framework of postmenopausal symptoms.

To accomplish this therapy with the use of technical measures which are simpler to achieve, the beta blocker dosage forms are presented such that they are placed in packages which are provided to obtain borderline active beta blocker concentrations for the treatment of vegetative symptoms, in particular with the ingestion and design characteristics of single doses, each of which produces a therapeutic effect for a plurality of days.

To reduce the proportion of direct central nervous effects, hydrophilic beta blockers in particular are used, preferably atenolol, nadolol, and sotalol.

The advantages obtained with the invention include, in particular, that with these borderline active dosage forms the beta blocker therapy of vegetative symptoms and syndromes can be therapeutically safer and their therapeutic spectrum of application can be expanded. The use of beta blockers, e.g., for the therapy of sleep disturbances in vegetative syndromes, has not been possible in this manner in the past with the prior art dosage forms for beta blockers.

Through the invention borderline active dosage forms of beta blockers, it is also possible in particular to significantly reduce the use of therapies acting on the central nervous system with tranquilizers and barbiturates, which include numerous adverse and residual effects. Even the associated potential for addictive risks with these substances can be reduced.

Compared to customary oral dosage forms of beta blockers, the invention borderline active dosage forms of beta blockers also open the possibility of carrying out short-term therapies with transient vegetative symptoms without the danger of cardiovascular withdrawal phenomena. The borderline active dosage forms of beta blockers thus produce only a reduction of adrenergically stimulated reactions but no persistent effects on basal cardiovascular rest values, as is the case with customary dosage forms of beta blockers.

In particular, compared to customary dosage forms of beta blockers, with the invention borderline active dosage forms of beta blockers the obligation to extend the application phase longer than is therapeutically necessary even in the therapy of transient vegetative symptoms and syndromes is eliminated.

Overall, compared to the customary dosage forms of beta blockers, with the invention borderline active dosage forms of beta blockers, the therapeutic risk-benefit ratio in the treatment of vegetative symptoms is significantly improved, for example, with regard to the performance capability and the quality of life of the patients, with regard to adverse effects on lipid and glucose metabolism, with accompanying problems such au reduced renal function with elderly patients and also in the therapy of child patients.

The dosages of beta blockers useful in the present invention are dependent on the route of administration. Oral dosages for vegetative symptoms preferably are in the range of from 10% to 50% of the currently lowest administered single dose as administered for a chronic use with the respective betablocker, including 15%, 20%, 25%, 30%, 35%, 40% and 45% and all ranges therebetween. Typical oral single doses are in the range, e.g., for Atenolol: of 2.5 to 12.5 milligrams, for Nadolol: 6 to 30 milligrams and for Sotalol: from 8 to 40 milligrams. These single doses can be administered in dosage intervals from 24 hours to 52 hours to treat vegetative symptoms.

Transdermal applications need higher loading doses for the transdermal system. This is due to the different bioavailability provided by this special route of administration compared to oral application. Transdermal systems do not liberate their complete loading dose. The higher concentration of the loading dose is in transdermal systems technically necessary to induce a suitable thermodynamic drive for the percutaneous diffusion process. In general the transdermal application needs similar dosages as the conventional oral does to induce borderline concentrations. The single loading dose in a transdermal patch is for the betablocker Mepindolol in a range of 5 to 20 milligrams.

A 20 mg Mepindolol loading does in a transdermal patch provided, for 24 hours, continuous serum concentrations of 0.5–2 nanograms/ml (C. de. Mey et al, Transdermal Delivery of Mepindolol and Propranolol in Normal Man, Arzneim. Forsch/Drug Res. 39 (II) 150 g (1989) incorporated herein by reference, compared to a transient peak serum concentration of more than 50 nanograms/ml with the same dosage in a tablet (Krause, W., Schwartzkopff, W., Plasma levels of Mepindolol in Healthy Volunteers after Oral Doses of Mepindolol Sulphate, Arzneim. Forsch./Drug Res. 33 (II) 1306 (1983) incorporated herein by reference.

For transdermal forms it is necessary to evaluate the individual loading dose empirically for each betablocker, due to their different physico-chemical properties, according to art accepted techniques. A technical composition suitable for the transdermal betablocker application of mepindolol is described in U.S. Pat. No. 4,765,986 incorporated herein by reference.

Different doses of same oral betablocker forms of the same betablocker are dose related absorbed and produce clear dose-concentration relations, which permit direct comparisons. The duration and the expression of the effect of the betablocker depends on the dose and biological affinity to the receptor. Therefore the invention oral betablocker borderline forms can be manufactured in conventional form according to the state of the pharmaceutical art by an ordinary skilled person in this field. The production of a borderline dose form is the same procedure as for a conventional oral form, but the oral borderline active forms contain only dosages in a range of 10% to 50% of the dosages of the respective usual oral betablocker form as they are administered for conventional oral use in chronic therapy in manifest diseases.

This application is based on German application P4334919.6 filed Oct. 13, 1993 incorporated herein in its entirety by reference. Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A method of effecting short-term therapy of transient functional cardiovascular symptoms, comprising administering to a patient in need thereof a borderline active dosage form of beta blockers, which produces in a patient only borderline active concentrations of active agent which produce no significant changes in physiological values in a cardiovascular system under resting conditions for the beta blocker used and which significantly reduces adrenergically induced transient stimulation effects from a pharmacodynamic standpoint, and wherein said dosage form is an oral dosage form, containing 10% to 50% of the currently administered lowest oral therapeutic single dose of the respective beta blocker which is given in a chronic therapy, and further wherein one dosage is administered about every 24 to 52 hours.

2. The method of claim 1, wherein said dosage comprises a hydrophilic beta blocker selected from the group consisting of atenolol, nadolol, and sotalol and which contain as a respective single oral dose for atenolol, a range of 2.5 to 12.5 milligrams; for nadolol, 6 to 30 milligrams; and for sotalol, 8 to 40 milligrams.

3. A method for treating sleep disturbances, comprising administering to a patient in need thereof a borderline active dosage form of beta blockers, which produces in a patient only borderline active concentrations of active agent which produce no significant changes in physiological values in the cardiovascular system under resting conditions for the beta blocker used and which significantly reduces adrenergically induced transient stimulation effects from a pharmacodynamic standpoint, and wherein said dosage form is an oral dosage form, containing 10% to 50% of the currently administered lowest oral therapeutic single dose of the respective beta blocker which is given in a chronic therapy, and
further wherein one dose is administered about every 24 to 52 hours.

4. The method of claim 3, wherein said dosage comprises a hydrophilic beta blocker selected from the group consisting of atenolol, nadolol, and sotalol, and which contains as a respective single oral dose for atenolol, a range of 2.5 to 12.5 milligrams; for nadolol, 6 to 30 milligrams; and for sotalol, 8 to 40 milligrams.

5. A method of effecting short-term therapy of transient functional cardiovascular symptoms, comprising administering to a patient in need thereof a borderline active dosage form of beta blockers, which produces in a patient only borderline active concentrations of active agent which produce no significant changes in physiological values in a cardiovascular system under resting conditions for the beta blocker used and which significantly reduces adrenergically induced transient stimulation effects from a pharmacodynamic standpoint, and wherein said dosage form is a transdermal dosage form, containing such a loading dose of the beta blocker in the transdermal system, which produces a serum concentration in a range of 10% to 50% of the serum concentration which is produced by the lowest therapeutic oral dosage of the respective beta blocker.

6. The method of claim 5, wherein said dosage comprises a hydrophilic beta blocker selected from the group consisting of atenolol, nadolol, and sotalol and which contain as a respective single oral dose for atenolol, a range of 2.5 to 12.5 milligrams; for nadolol, 6 to 30 milligrams; and for sotalol, 8 to 40 milligrams.

7. A method for treating sleep disturbances, comprising administering to a patient in need thereof a borderline active dosage form of beta blockers, which produces in a patient only borderline active concentrations of active agent which produce no significant changes in physiological values in the cardiovascular system under resting conditions for the beta blocker used and which significantly reduces adrenergically induced transient stimulation effects from a pharmacodynamic standpoint, and wherein said dosage form is a transdermal dosage form, containing such a loading dose of the beta blocker in the transdermal system, which produces a serum concentration in the range of 10% to 50% of the serum concentration which is produced by the lowest therapeutic oral dosage of the respective beta blocker.

8. The method of claim 7, wherein said dosage comprises a hydrophilic beta blocker selected from the group consisting of atenolol, nadolol, and sotalol, and which contains as a respective single oral dose for atenolol, a range of 2.5 to 12.5 milligrams; for nadolol, 6 to 30 milligrams; and for sotalol, 8 to 40 milligrams.

* * * * *